US006528107B2

(12) United States Patent
Chinn et al.

(10) Patent No.: US 6,528,107 B2
(45) Date of Patent: Mar. 4, 2003

(54) METHOD FOR PRODUCING ANTIMICROBIAL ANTITHROMBOGENIC MEDICAL DEVICES

(75) Inventors: Joseph A. Chinn, Austin, TX (US); Richard E. Phillips, Jr., San Marcos, TX (US); Joseph A. Sauter, Austin, TX (US); R. Michael Casanova, Austin, TX (US); Chandrashekhar P. Pathak, Austin, TX (US); Mark A. Moore, Austin, TX (US); L. Diane Bruce, Round Rock, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 199 days.

(21) Appl. No.: 09/359,235

(22) Filed: Jul. 22, 1999

(65) Prior Publication Data

US 2001/0003599 A1 Jun. 14, 2001

Related U.S. Application Data

(63) Continuation-in-part of application No. 09/232,922, filed on Jan. 19, 1999, now abandoned.

(51) Int. Cl.[7] .......................... A61L 15/00; A61L 27/00
(52) U.S. Cl. ..................... 427/2.24; 427/2.3; 427/2.31
(58) Field of Search .................. 427/430.1, 421, 427/2.24, 2.25, 2.26, 2.27, 2.28, 2.29, 2.3, 2.31

(56) References Cited

U.S. PATENT DOCUMENTS

| | | | |
|---|---|---|---|
| 3,511,684 A | 5/1970 | Huffaker | 117/47 |
| 3,585,647 A | 6/1971 | Gajewski et al. | 3/1 |
| 4,107,121 A | 8/1978 | Stoy | 260/29.6 |
| 4,254,180 A | 3/1981 | Kline | 428/323 |
| 4,326,532 A | 4/1982 | Hammar | 128/349 |
| 4,331,697 A | 5/1982 | Kudo et al. | 427/2 |
| 4,442,133 A | 4/1984 | Greco et al. | 427/2 |
| 4,521,564 A | 6/1985 | Solomon et al. | 525/54.1 |
| 4,526,714 A | 7/1985 | Feijen et al. | 260/112 |
| 4,600,652 A | 7/1986 | Solomon et al. | 428/423.3 |
| 4,634,762 A | 1/1987 | Feijen et al. | 530/350 |
| 4,642,242 A | 2/1987 | Solomon et al. | 427/2 |
| 4,676,974 A | 6/1987 | Hofmann et al. | 424/9 |
| 4,678,660 A | 7/1987 | McGary et al. | 424/25 |
| 4,678,671 A | 7/1987 | Feijen et al. | 424/443 |
| 4,749,585 A | 6/1988 | Greco et al. | 427/2 |
| 4,895,566 A | 1/1990 | Lee | 604/266 |
| 4,917,686 A | 4/1990 | Bayston et al. | 604/265 |
| 4,952,419 A | 8/1990 | De Leon et al. | 427/2 |
| 4,973,493 A | 11/1990 | Guire | 427/2 |
| 4,979,959 A | 12/1990 | Guire | 623/66 |
| 5,053,453 A | 10/1991 | Ku | 525/54.1 |
| 5,103,306 A | 4/1992 | Weiman et al. | 358/133 |
| 5,104,407 A | 4/1992 | Lam et al. | 623/2 |
| 5,217,493 A | 6/1993 | Rand et al. | 623/11 |
| 5,263,992 A | 11/1993 | Guire | 623/66 |
| 5,308,641 A | 5/1994 | Cahalan et al. | 427/2 |
| 5,414,075 A | 5/1995 | Swan et al. | 568/333 |
| 5,451,424 A | * 9/1995 | Solomon et al. | 427/2.1 |
| 5,512,329 A | 4/1996 | Guire et al. | 427/508 |
| 5,562,922 A | * 10/1996 | Lambert | 424/486 |
| 5,567,495 A | * 10/1996 | Modak et al. | 428/36.9 |
| 5,624,704 A | 4/1997 | Darouiche et al. | 427/2.24 |
| 5,679,659 A | 10/1997 | Verhoeven et al. | 514/56 |
| 5,716,397 A | 2/1998 | Myers | 623/2 |
| 5,741,551 A | 4/1998 | Guire et al. | 427/407.1 |
| 5,865,814 A | 2/1999 | Tuch | 604/265 |
| 5,877,263 A | 3/1999 | Patnaik et al. | 525/453 |

OTHER PUBLICATIONS

US 5,556,632, 09/1996, Kohler et al. (withdrawn)
Raad, I. et al., Effect of Anti–Infective Coatings on Biofilms, Surfaces in Biomaterials Foundation, 1996, pp. 4–9.
Sherertz, R. J., Efficacy of Dicloxacillin–Coated Polyurethane Catheters in Preventing Subcutaneous Staphylococcus Aureus Infection in Mice, Antimicrobial Agents and Chemotherapy, Aug. 1989, pp. 1174–1178.
Clapper, D. L., et al., Hirudin Immobilization to Produce Anitihombic Surfaces, Cardiovascular Science and Technology: Basic and Applied, Dec. 1–3, 1990.
Anderson, A. B., et al., Photochemical Immobilization of Heparin to Reduce Thrombogenesis, The 20th Annual Meeting of the Society for Biomaterials, Apr. 5–9, 1994, p. 75.
Hirudin Immobilization to Produce Antithrombic Surfaces, Cardiovascular Science and Technology: Basic and Applied Dec. 1–3, 1990.

* cited by examiner

Primary Examiner—Shrive P. Beck
Assistant Examiner—Jennifer Kolb Michener
(74) Attorney, Agent, or Firm—Timothy L. Scott

(57) ABSTRACT

A method is provided for producing antimicrobial, antithrombogenic medical devices. The method employs an antimicrobial treatment process wherein an antimicrobial agent is dissolved in an appropriate solvent and the resulting solution is contacted with a portion of a medical device of interest. The antimicrobial treatment process is advantageously performed without the need for additional compounds to facilitate antimicrobial agent uptake into the device. The method further comprises an antithrombogenic treatment process wherein antithrombogenic agents or materials are applied or otherwise associated with at least some portion of the medical device.

20 Claims, No Drawings

METHOD FOR PRODUCING ANTIMICROBIAL ANTITHROMBOGENIC MEDICAL DEVICES

This application is a continuation-in-part application of U.S. patent application Ser. No 09/232,922, filed on Jan. 19, 1999 now abandoned.

BACKGROUND OF THE INVENTION

1. Field of the Invention

This invention relates generally to medical devices intended for implantation into humans. More particularly, this invention concerns methods for providing medical devices which can inhibit microbial infection and thrombogenesis on or near the medical device after its implantation into the body.

2. Description of the Related Art

Implantable medical devices have become critical in the management of a variety of human diseases and other conditions. Colonization of microorganisms on the surfaces of such medical devices following implantation occurs relatively infrequently, but can produce serious and costly complications, including the need to remove and/or replace the implanted device and/or vigorous treatment of secondary infections.

Although infection of implanted medical devices is a relatively infrequent complication associated with their clinical use, the threat to infected patients, and the cost to the medical care system, are significant. For example, in heart valve replacement surgery, one of the most serious complications is prosthetic valve endocarditis (PVE). Prosthetic valve endocarditis is a result of bacterial infection at the junction of the sewing cuff and annulus, or in the valve sewing cuff itself. Although the overall frequency of PVE is only about 1% per patient year, the condition is associated with high morbidity and mortality (up to 60%).

Approaches for controlling infections associated with implanted medical devices have had only limited success. For example, although coating a material with immobilized antimicrobial compounds has been reported to effectively reduce bacterial colonization of devices in a laboratory setting, similar results have been difficult to replicate in the clinical setting. To be effective in vivo, antimicrobial agents immobilized on the surface of a medical device need to intimately contact the colonizing bacteria that has infected the device. Unfortunately, many clinically relevant bacteria produce a slimy protective substance called biofilm within which they grow. This biofilm, among other things, prevents direct contact of the bacterial cells with a substrate surface to which they adhere, making the bacteria resistant to otherwise toxic materials that may be present on the substrate surface.

In the laboratory, the antimicrobial efficacy of medical devices that have been treated in one way or another in attempt to confer some degree of antimicrobial activity to the device, has often been evaluated by exposing the devices to bacterial cultures. The selection and source of bacteria for such testing is critical to obtaining meaningful results, since it is now known that microorganisms floating free in a cell culture (called planktonic bacteria) behave differently than those adherent to a substrate, such as a bacterial culture vessel or an implanted medical device. Planktonic bacteria are more susceptible to antimicrobial agents immobilized on a surface than are biofilm-producing bacteria. Thus, devices coated with immobilized antimicrobial agents may effectively prevent colonization of planktonic bacteria in the laboratory, but may be completely ineffective in preventing infection of devices by clinically relevant biofilm-enclosed bacteria. As a result, the experimental use of planktonic bacteria cultured in the laboratory, rather than biofilm bacteria derived from clinical infections, has led to the commercialization of numerous medical devices lacking clinical efficacy.

To effectively inhibit biofilm bacterial growth, an antimicrobial agent should penetrate the biofilm. To achieve this, the antimicrobial agent must be able to diffuse from the surface of the medical device following implantation. Therefore, antimicrobial agents immobilized on the surface of a medical device, and therefore not subject to diffusion, are largely ineffective against many clinically relevant microorganisms. A more effective medical device will have the ability to deliver diffusable antimicrobial agent to the local environment following implantation.

Various methods have been described for coating or otherwise incorporating antimicrobial agents into or onto medical devices in a manner which allows for their release into the local environment of an implanted medical device. U.S. Pat. No. 5,624,704 reports a method for impregnating a non-metallic medical implant with an antimicrobial agent by first dissolving the antimicrobial agent in an organic solvent to form an antimicrobial composition. Thereafter, a separate penetrating agent and alkalinizing agent must be added to the antimicrobial composition. The antimicrobial composition is then applied to a medical device of interest in order to cause the incorporation of the composition into the material of the medical device. Thus, the method of U.S. Pat. No. 5,624,704 teaches the necessity of using additional components, i.e., penetrating and alkalinizing agents, in a dissolved antimicrobial composition, in order to achieve effective incorporation into the medical device. Unfortunately, the use of these additional components can substantially increase the materials and processing costs associated with such a method, and can also lead to degradation of the antimicrobial agents.

In addition to the problems of microbial infection discussed above, other complications associated with the use of many implantable medical devices stem from the complex cellular and humoral reactions which occur when a foreign material comes into contact with blood and/or other physiological fluids. Among the most significant of these are the rapid thrombogenic actions which can occur following implantation of a medical device. Initial contact of a device with blood results in deposition of plasma proteins, such as albumin, fibrinogen, immunoglobulin, coagulation factors, and complement proteins. The cellular activities which follow can, among other things, lead to vascular constriction which can hinder blood flow, and inflammatory reactions which can damage or impair the function of a medical device. A variety of methods and compositions have been reported for increasing the thromboresistance of medical device surfaces by bonding or incorporating into or onto the device one or more antithrombogenic agents, such as heparin, hirudin, albumin, phospholipids, streptokinase, tissue plasminogen activator (TPA) or urokinase, hydrophilic polymers such as hyaluronic acid, chitosan, methyl cellulose, and poly(ethylene oxide), poly(vinyl pyrrolidone), growth factors such as endothelial cell growth factor, epithelial growth factor, osteoblast growth factor, fibroblast growth factor, platelet derived growth factor (PDGF), and angiogenic growth factor, and other proteins, carbohydrates and fatty acids.

The present invention is directed to providing medical devices which have both antimicrobial and antithrombogenic properties for overcoming, or at least reducing the effects of, one or more of the problems set forth above.

SUMMARY OF THE INVENTION

According to one aspect of the present invention, a method is provided for producing a medical device having antimicrobial and antithrombogenic properties. The method, in a first treatment process, comprises dissolving one or more antimicrobial agents in a suitable solvent, such as an alcohol, ether, aldehyde, acetonitrile, or combinations thereof, to form an antimicrobial solution. The antimicrobial solution is thereafter contacted with at least a portion of a medical device under conditions effective for causing incorporation of the antimicrobial agent into or onto the portion of the medical device contacted by the antimicrobial solution. The method further comprises a second treatment process, which may be performed before, after, or in some situations simultaneous with, the first treatment process described above, wherein the medical device is treated in a manner that provides an antithrombogenic agent or material in or on at least a portion of the medical device. As a result, the portion of the medical device so treated exhibits antithrombogenic properties, i.e., has a reduced propensity for eliciting a thrombogenic response following implantation of the device, compared with a similar device which has not been subjected to the antithrombogenic treatment.

The incorporation of the antimicrobial agent into or onto the medical device is advantageously achieved without the need for additional components in the antimicrobial solution, i.e., penetrating agents, alkalinizing agents, etc., in order to achieve incorporation of the antimicrobial agent into or onto the device. The antimicrobial agent incorporated into a medical device according to this invention nonetheless exhibits clinically desirable antimicrobial release kinetics from the medical device after exposure to an in vivo environment.

In yet a further aspect of the present invention, medical devices are provided which have antimicrobial and antithrombogenic agents and/or materials present on at least some portion of the devices. Consequently, the medical devices provided by this invention are less susceptible to microbial colonization and thrombogenic activity following implantation of the devices in vivo.

DETAILED DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

According to the present invention, a method is provided for incorporating one or more antimicrobial and antithrombogenic agents into or onto a medical device. This method employs a first treatment process which comprises dissolving an antimicrobial agent or agents in a suitable solvent system to form an antimicrobial solution and contacting the antimicrobial solution with at least a portion of a medical device for a duration and under conditions effective to allow the incorporation of antimicrobial agent into or onto the medical device. The method of the invention, in an additional treatment process, involves treating the device under conditions effective for incorporating one or more antithrombogenic agents and/or materials into or onto at least some portion of the device.

The phrases "incorporation into" and "incorporating into," as used herein, means that at least some antimicrobial agent and/or antithrombogenic agent permeates, adheres to, or otherwise becomes associated with one or more of the polymeric structures of which the medical device is comprised. Thus, the antimicrobial and/or antithrombogenic agent may be largely associated with the surface of the device, as in a coating, may penetrate within or between the polymeric structure that makes up the device, may be covalently or ionically bound to the device structure, etc. The nature of the association between the antimicrobial agent the antithrombogenic agent and the medical device may depend on the particular agent used, the antimicrobial and antithrombogenic treatment processes employed, and/or the type and structure of the medical device being treated.

The extent of incorporation of the agents or materials into or onto a medical device may be evaluated by any of a number of approaches. For example, the incorporation may be assessed by mass analysis of the device before and after treatment. Alternatively, the incorporated agent may be extracted or otherwise removed from the device using an appropriate method and analyzed by a suitable quantitative technique, e.g., high-performance liquid chromatography or ultraviolet/visible spectroscopy. The extent and effectiveness of incorporation may also be evaluated by more functional approaches, i.e., wherein antimicrobial and/or antithrombogenic activities are assayed by suitable in vitro or in vivo testing.

The medical device used in accordance with the method of this invention is not limiting and may be selected from any one of the numerous device types available to the medical practitioner, including cardiovascular devices, orthopedic implants, and a variety of other prosthetic devices. Examples of such devices may include, but are not limited to, annuloplasty rings, heart valve sewing cuffs, catheter sewing cuffs, pericardial patches, vascular grafts, wound dressings, sutures, pledgets, and other like devices. Additional examples may include fixator pins, femoral prostheses, acetabular prostheses, dental prostheses, and the like.

ANTIMICROBIAL TREATMENT

"Antimicrobial agent", as used herein, refers to essentially any antibiotic, antiseptic, disinfectant, etc., or combination thereof, effective for inhibiting the viability and/or proliferation of one or more microorganisms. Numerous classes of antibiotics are known and may be suitable for use in accordance with this invention. Such antibiotics may include, but are not necessarily limited to, tetracyclines (e.g., minocycline), rifamycins (e.g., rifampin), macrolides (e.g., erythromycin), penicilins (e.g., nafcillin), cephalosporins (e.g., cefazolin), other beta-lactam antibiotics (e.g., imipenem and aztreonam), aminoglycosides (e.g., gentamicin), chloramphenicol, sufonamides (e.g., sulfamethoxyazole), glycopeptides (e.g., vancomycin), quinolones (e.g., ciprofloxacin), fusidic acid, trimethoprim, metronidazole, clindamycin, mupirocin, polyenes (e.g., amphotericin B), azotes (e.g., fluconazole), beta-lactam inhibitors, etc.

Examples of illustrative antibiotic agents that may be used in accordance with the present invention include minocycline, rifambin, erythromycin, nafcillin, cefazolin, imipenem, aztreonam, gentamycin, sulfamethoxazole, vanomycin, ciprofloxacin, trimethoprim, metronidazole, clindamycin, telcoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, and other like compounds. The antibiotics used in accordance with this invention will generally be selected so as to have relatively low water solubility such that their period of dissolution into the body is prolonged. Moreover, it may be desired for many applications that one or more antimicrobial agents having distinct modes of action are incorporated into the medical device in order to broaden its range of antimicrobial activity.

Suitable antiseptics and disinfectants for use in this invention may include, for example, hexachlorophene, cationic bisiguanides (e.g., chlorohexidine, chclohexidiene, etc.), iodine and iodophores (e.g., povidone-iodine), para-chloro-meta-xylenol, furan medical preparations (e.g., nitrofurantoin, nitrofurazone), methenamine, aldehydes (glutaraldehyde, formaldehyde, etc.), alcohols, and the like.

In one illustrative embodiment of the present invention, the antimicrobial agent used to treat a medical device according to this invention is comprised of minocycline, rifampin, or a mixture thereof. Minocycline is a semisynthetic antibiotic derived from tetracycline that functions by inhibiting protein synthesis. Rifampin is a semisynthetic derivative of rifamycin B, a macrocyclic antibiotic compound produced by the mold, *Streptomyces mediterranic*. Rifampin inhibits bacterial DNA-dependent RNA polymerase activity and is bactericical in nature. Both minocycline and rifampin are commercially available, are soluble in numerous organic solvents, and are active against a wide range of gram-positive and gram-negative organisms.

In order to incorporate an antimicrobial agent or agents into a medical device, the desired antimicrobial agent or agents are first dissolved in an appropriate solvent or combination of solvents to form an antimicrobial solution. Suitable solvents in this regard include essentially any aqueous or organic solvent(s) that will effectively dissolve the antimicrobial agent or agents of interest, and that are conducive with the incorporation of the at least some of the dissolved antimicrobial agent into the medical device. The solvent is generally selected from one that will readily spread onto and/or along the particular medical device surface to which it is applied. The degree of this spreading may be influenced by the surface tension of the solvent and by the surface characteristics and configuration of the material used to produce the medical device. According to this invention, the incorporation of the antimicrobial agent into the medical device occurs in the substantial absence of additional constituents, e.g., penetrating agents, alkalinizing agents, etc., that have been conventionally used for facilitating antimicrobial agent penetration and/or adherence into or onto the medical device. Illustrative examples of suitable solvents for use in this invention include, but are not necessarily limited to, $C_1$ to $C_6$ organic solvents such as $C_1$ to $C_6$ alcohols (e.g., methanol, ethanol, etc.), $C_1$ to $C_6$ ethers (e.g., tetrahydrofuran), $C_1$ to $C_6$ aldehydes, aprotic heterocyclics (e.g., n-methyl pyrrolidinone, dimethyl sulfoxide, dimethyl formamide), acetonitrile, and acetic acid.

The concentration of the antibiotic agent in the antibiotic solution is not specifically restricted. Optimal concentration ranges will likely vary depending upon the particular antimicrobial agent/solvent system used, on the conditions under which the antimicrobial solution is contacted with the medical device, and on the medical device being treated, but can nonetheless be readily determined by the skilled individual in the art. In general, a higher concentration of an antimicrobial agent in the antimicrobial solution will result in greater incorporation into or onto the medical device under an otherwise constant set of application conditions. However, an upper concentration limit will typically characterize a particular combination of antimicrobial solution and medical device, above which further antimicrobial incorporation will become limited. Generally, the concentration of the antimicrobial agent in the antimicrobial solution is essentially in the range of about 1 mg/ml to 60 mg/ml for each antimicrobial agent present in the composition.

The antimicrobial solution of the present invention is applied to, or otherwise contacted with, at least some portion of the medical device of interest in order to effect incorporation of the antimicrobial agent into the device. As will be apparent to the skilled individual in this art, the means by which the antimicrobial solution is contacted with the medical device is not critical, and may vary depending on the type of device being treated, the area of the device being treated, etc. Typically, the medical device will simply be dipped or otherwise immersed in an antimicrobial solution. Alternatively, the antimicrobial solution may be applied to the device or area of the device being treated, e.g., by injection, flushing, spraying, etc. Other techniques for contacting the antimicrobial solution with the medical device will be readily apparent to the skilled individual in this art.

Subsequent to contacting the antimicrobial solution with the medical device, the antimicrobial solution is generally allowed to remain in contact with the device for a duration and under conditions effective to cause a desired degree of incorporation of the antimicrobial agent into or onto the medical device.

The temperature of the solution during this treatment step is not critical, and can be essentially any temperature which does not adversely effect the desired antimicrobial agent incorporation. Excessively high temperatures should be avoided if they are in a range which can cause degradation of the antimicrobial agent. Furthermore, care should be taken when treating the device at temperatures that are sufficiently low since they may adversely impact the solubility of the antimicrobial agent(s) in the antimicrobial solution. A desired treatment temperature will typically be in the range of about 10 deg.C to about 60 deg.C, more typically it will be in the range of about 20 deg.C to about 50 deg.C. The duration of the medical device treatment step is not specifically restricted, and may be in the range of 0.1 minutes to several hours or more. Typically, treatment duration in the range of about 0.1 hours to about 2 hours will result in a desirable degree of antimicrobial agent incorporation into a medical device. Of course, the optimal treatment time for a given application may vary depending on a number of parameters, e.g., the antimicrobial solution being used, reaction temperature, etc., but this can be readily determined by one skilled in the art.

The treated device is typically dried to eliminate any remaining solvent, e.g., by air-drying, heating, etc. After drying, the antimicrobial agent incorporated into or onto the device is not subject to substantial diffusion until implanted in vivo, or otherwise exposed to comparable environment, wherein the incorporated antimicrobial agent becomes redissolved, and therefore more subject to diffusion from the device into the surrounding environment.

Medical devices for use according to this invention may include essentially any device wherein effective incorporation and/or precipitation of an antibiotic agent can be achieved using the disclosed antimicrobial solutions and wherein that incorporation does not adversely effect the resulting efficacy of any prior or subsequent process for incorporating one or more antithrombogenic agents. These may include medical devices comprised of thermoplastic or polymeric materials such as rubber, plastic, polyethylene, polyurethane, silicone, polytetrafluoroethylene, polyethylene terepthalate, latex, elastomers, and other like materials. These may also include metals (e.g., titanium, cobalt-chromium, stainless steel) and ceramics (hydroxyapetite, pyrolytic carbon) in cancellous, i.e., porous, configurations.

The medical devices will frequently contain at least some materials in a fabric or fabric-like form, having polymeric fibers comprised of polytetrafluoroethylene, polyethylene terepthalate, and other like materials. Examples of such devices which contain at least some of these materials may include, but are not limited to, annuloplasty rings, heart valve sewing cuffs, catheter sewing cuffs, pericardial patches, vascular grafts, would dressings, sutures, pledgets, etc. It was unexpected that the antimicrobial solutions of this invention would adequately spread along and within the polymeric fiber structures of such devices to an extent effective to achieve a desirable antimicrobial agent incorporation and release profile.

By practice of the antimicrobial treatment process of the present invention, a medical device is provided which exhibits the release of antimicrobial agent from the device for some period of time after the device has been exposed to an in vivo environment The release profile of the antimicrobial agent from the device may be evaluated using any one of a variety of approaches. For example, this may involve sequentially monitoring over time the diffusion of antimicrobial agent from the device into a solution in which the device is immersed. The solution may be replaced at certain time points, and the quantity of antimicrobial agent evaluated at the various time points by a suitable analytic technique, such as high-performance liquid chromatography.

The medical device treated in accordance with this invention will preferably exhibit antimicrobial activity, i.e., the antimicrobial agent is released from the device at sufficient levels to inhibit the growth of antimicrobial organisms adherent to the device or in close proximity thereto. The antimicrobial activity of the device resulting from release of the antimicrobial agent may be evaluated by a variety of approaches. For example, zone of inhibition (ZOI) analyses, and other similar variations thereof, may be used (see, for example, Sherertz, et al. Antimicrobial Agents and Chemotherapy, August 1989, p.1174, 1989). Using this approach, a medical device is placed directly on an agar plate covered with growing bacteria. The plates are evaluated over time to determine the extent of bacterial growth in the agar surrounding the device. A bacterial free zone surrounding the sewing cuff, called a zone of inhibition, is indicative of inhibition of bacterial growth by agents that have diffused from a treated medical device into the surrounding agar.

The antimicrobial release and/or activity from the medical device is generally sustained for an extended number of days, or even weeks. In this way, the susceptibility to medical device infection may be inhibited for a clinically relevant duration following device implantation in vivo. In an illustrative embodiment of the invention, the medical device of this invention will exhibit some degree of antimicrobial release and/or activity for at least a day, more typically for several days, and in some instances for up to a week or more, following exposure to an in vivo environment.

ANTITHROMBOGENIC TREATMENT

"Antithrombogenic," as this term is used herein in reference to the medical devices produced according to the present invention, is intended to encompass essentially any medical device which has been treated under conditions effective for incorporating into or onto at least some portion of the device, either directly or indirectly, the desired antithrombogenic agent(s) and/or material(s). As a result, the portion of the device treated by this antithrombogenic treatment process will preferably exhibit some degree of antithrombogenic activity, as determined, for example, by its ability to inhibit thrombin-catalyzed fibrin clot formation, its ability to inhibit the amidolytic activity of thrombin, or by its ability to cause a substantial reduction in other known measures of the thrombogenic response when compared with a medical device that has not been so treated.

Antithrombogenic agents are well known and readily available to the individual skilled in this art. Examples of antithrombogenic or nonthrombogenic agents and materials suitable for use in accordance with this invention may include or be at least partly comprised of heparin, hirudin, albumin, phospholipids, streptokinase, tissue plasminogen activator (TPA), urokinase, hydrophilic polymers such as hyaluronic acid, chitosan, methyl cellulose, poly(ethylene oxide), poly(vinyl pyrrolidone), growth factors such as endothelial cell growth factor, epithelial growth factor, osteoblast growth factor, fibroblast growth factor, platelet derived growth factor (PDGF), and angiogenic growth factor, other like compounds, and functionally equivalent variants and/or derivatives thereof.

The approach by which an antithrombogenic agent is incorporated into or onto some or all of a medical device is not limiting, and may be selected from any of a number of methods available in the art, some illustrative examples of which are described below.

For example, U.S. Pat. No. 5,679,659, assigned to Medtronic Inc., the disclosure of which is incorporated herein by reference, describes a method for making a heparinized medical device. In this method, heparin is reacted with a periodate compound and this mixture is reacted and then applied to immobilized amine groups on a medical device surface. The application to the immobilized amine groups causes a reaction between the aldehyde groups on the heparin and the immobilized amine groups to form a Schiff base. A mild reducing agent is used to stabilize the Schiff base into a secondary amine.

The amine groups may be provided on the medical device surface by methods known to those skilled in the art. For example, amine-functional spacer molecules have been used to immobilize biomolecules. The spacer insures that the active site of the biomolecule is held outward away from the support so as to contact the body fluid efficiently. The spacers are derived from organic molecules having at least two reactive functional groups generally situated at opposing ends of the molecule. Such groups serve as attachment vehicles capable of coupling the spacer to the solid surface and to the biomolecule.

The immobilized amine functionality is generally provided in a manner similar to that disclosed in U.S. Pat. No. 5,308,641 in which a polyalkyleneimine is covalently attached to a substrate. Polyalkyleneimine is intended to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkyleneimines are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used.

An important aspect of this heparin immobilization process is the controlled oxidation of the heparin molecules to provide a limited number of reactive aldehyde groups on the average heparin molecule. This is accomplished by adding a periodate to a buffered aqueous solution of the heparin and allowing it to react with the heparin. Any water soluble periodate can be used but preferably the periodate is an alkali metal periodate such as sodium periodate. If the periodate used is sodium periodate and the heparin used is a commercially available injectable form of heparin (i.e. its sodium salt with activity of about 160 u/mg), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

In another example of a method for providing an antithrombogenic agent on a medical device, U.S. Pat. No. 5,865,814, assigned to Medtronic Inc., the disclosure of which is incorporated herein by reference, describes an approach whereby an aqueous heparin solution is applied to a stent device and the water is allowed to evaporate, thereby leaving on the stent surface a coating of heparin. Typically, the solution can be applied by either spraying the solution onto the device or immersing the device in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the device. In either a coating applied by spraying or by immersion, multiple application steps are generally desirable to provide optimal coating uniformity and improved control over the amount of antithrombogenic agent to be applied to the device.

In order to provide control over the elution of heparin from the device when using this approach, a porous polymeric overlayer may also be applied to the device. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response.

With an aqueous coating of heparin is provided on the device, the polymer overlayer is important in controlling the elution from the implanted device since the heparin is water soluble and would otherwise elute immediately without providing a desired long term benefit. For example, an aqueous coating of heparin can be provided by spraying a solution or dispersion of heparin onto the device body. When the applied heparin layer is dry, a solution of chloroform and poly(L-lactic acid) could be used to form the overlayer by spraying the polymer solution onto the device as disclosed above.

The overlayer is preferably provided in porous form. A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-lactic acid) as the polymer, a suitable solvent composition can include about a 40/60% (w/w) isooctane/chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly (L-lactic acid) solution). This mixture is then applied to the device. It will be appreciated by those skilled in the art that the nature of the ingredients and the relative concentrations of the ingredients will determine the size of pores.

Other methods for providing antithrombogenic surfaces, for example as described in U.S. Pat. Nos. 5,512,329 and 5,741,551, the disclosures of which are incorporated herein by reference, and other related patents assigned to BSI Corporation, relate to methods for modifying substrate surfaces by bonding molecules, e.g., protein molecules, to substrates through external activation of latent reactive groups carried on the molecules. The latent reactive groups are groups which respond to specific applied external stimuli to undergo active specie generation with resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups are generally well known and may be chosen to be responsive to various portions of the electromagnetic spectrum.

Utilizing reactive chemical units bearing latent reactive groups, one will desirably first coat a surface or other substrate with a solvent solution of such molecules. Upon removal of solvent, the application of an appropriate external stimulus such as U.V. light will cause the molecules to covalently bond, through the latent reactive groups, to the substrate. The substrate may then be appropriately contacted with a solution containing the desired polymer, monomer or oligomer molecules to cause bonding to these molecules.

The loading density resulting from attachment of polymer molecules to a surface or other substrate in accordance with the above method may be regulated in several ways. First, the degree of activation of latent reactive groups is generally a function of the quantity of the external stimulus that is applied, and thus the extent of covalent bonding through the latent reactive groups may be regulated by regulating the intensity and time of application of the applied stimulus. Regulation of the applied stimulus is particularly easy when the stimulus is actinic radiation; one can readily regulate the amount of radiation to which the latent reactive groups are exposed. Loading density may also be regulated by adjusting the capacity of polymer molecules of the invention to bring their latent reactive groups into bonding proximity with a surface. Thus, one may regulate the viscosity of a solution of polymer molecules in an appropriate solvent as well as the solubility of polymer in the solvent.

Hirudin, a naturally occurring anticoagulant, has also been used to provide antithrombogenic surfaces. For example, European Patent Application No. 0 200 655 describes a method for treating materials for use in medical devices in which the surface is treated with a wetting solution of a palladium or rhodium salt and then treated with an anticoagulant such as heparin or hirudin under conditions to produce ionically bound coatings.

In addition, U.S. Pat. No. 5,053,453, assigned to Baxter Inc., the disclosure of which is incorporated herein by reference, describes coupling hirudin or hirudin derivatives either directly to the functional groups of a support material or by way of linking groups. The method generally comprises coupling the hirudin or hirudin derivative by a functional group of an amino acid residue to an active functional group of a substrate support material. The method for coupling is dependent upon several factors including the available functional groups on the support material, the coupling site or sites on the protein, biological activity of the resulting material, selectivity and efficiency of the coupling reaction.

For example, if the coupling site on the protein, i.e. the amino acid residue, is not in close proximity to the active site of the protein, i.e. the thrombin binding region, and the support material contains the appropriate active functional groups, the protein may be directly coupled to the support material utilizing reactions known to those skilled in the art. Alternatively, the protein can be coupled to the support material by a linking group. Examples of linking groups include bifunctional reagents such as bifunctional protein crosslinking reagents, polypeptides, proteins, protein segments, and multifunctional polymers such as polyethyleneimines or dendritic polymers. The choice of a linking group can depend on the coupling site, the functional groups of the support material, biological activity of the resulting material and the efficiency and selectivity of the coupling reaction. For example, the phenolic group of tyrosine can be modified using bifunctional reagents such as N-(4-diazobenzoyl)-N (3-maleimidopropionyl) hydrazine-tetrafluoroborate (DMHT) and N-succinimidyl-3-(2-pyridyldithio) propionate (SPDP) to add a sulfhydryl group for coupling with support materials which have active amino groups.

Conjugates of hirudin and support materials can be made according to this method using a variety of bifunctional protein crosslinking reagents. Examples of such reagents include SPDP, bifunctional derivatives of imidoesters such as dimethyl adipimidate and dimethyl suberimidate, active esters such as disuccinimidyl suberate, aldehydes such as glutaraldehyde and glycolaldehyde, bis-azido compounds such as bis-(p-azidobenzoyl) hexanediamine, bis-diazonium derivatives such as bis-(p-diazoniumbenzoyl)-ethylenediamine, diisocyanates such as tolylene-2,6-diisocyanate and tolylene-2,4-diisocyanate, and bis-active fluorine compounds such as 1,5-difluoro-2,4-dinitrobenzene and other reagents such as ethylene glycol/bis-[succinimidyl succinate], m-maleimido benzoyl sulfasuccinimide, and diethylene triamine pentacetic acid anhydride.

Where the biological activity of the protein would be greatly reduced by direct coupling due to steric hindrance, such as coupling at the C-terminal residue, or sticking of the protein to the support material, it can be desirable to use a linking group which would act to space the protein away from the support material. Examples of such linking groups include, but are not limited to, polypeptides, proteins and multifunctional polymers. Such linking groups can also provide multiple sites for attachment of the hirudin or hirudin derivatives to increase the binding efficiency.

In addition to the examples described above, many other antithrombogenic treatment methods are similarly known and available to the skilled individual in the art for use in conjunction with the medical devices of this invention, including, but not limited to, methods for providing substrate surfaces with agents such as heparin, e.g., U.S. Pat. Nos. 3,511,684, 3,585,647, 4,254,180, 4,331,697, 4,676,974, 4,526,714, 4,634,762, 4,678,660, 4,678,671 and 5,877,263, phospholipids, e.g., U.S. Pat. No. 5,556,632, chitosan, e.g., U.S. Pat. No. 4,326,532, antithrombogenic polymers, e.g., U.S. Pat. Nos. 4,521,564, 4,600,652 and 4,642,242, and others, e.g., U.S. Pat. Nos. 4,973,493, 4,979,959, 5,263,992, 5,414,075, 5,512,329 and 5,741,551, the disclosures of which are incorporated herein by reference.

The above approaches for incorporating antithrombogenic agents or materials into or onto substrate surfaces are described for illustrative purposes only. As will be apparent to the skilled individual, the particular method employed for providing an antithromobogenic medical device for use in this invention may be selected from any of a variety of conventional approaches. Of course, it will generally be desired that the antithrombogenic treatment process is selected and performed such that the process and resulting surface-modified product is compatible with and does not adversely effect any prior, subsequent or simultaneously performed antimicrobial treatment process according to this invention, or the antimicrobial properties of the device so produced.

The order in which the antimicrobial and antithrombogenic treatment processes are performed may be dictated by the specific objectives for a given application, but this order will typically not be critical. The preferred order may depend, for example, on the nature and composition of the particular medical device being treated, the antimicrobial and/or antithrombogenic agents or materials being used, the specific processes by which they are applied to the medical device, etc. For example, it may be preferred to perform the antithrombogenic treatment process prior to the antimicrobial treatment process in situations in which the antithrombogenic agents are to be covalently bound to a material of the medical device but wherein the antimicrobial agent(s) are bound largely by non-covalent interactions.

The following examples are provided to demonstrate certain illustrative embodiments of this invention. It should be appreciated by those skilled in the art that the techniques disclosed in the illustrative examples which follow represent those found by the inventors to function in the practice of the invention. However, those skilled in the art should, in light of the present disclosure, appreciate that many changes can be made in the specific embodiments which are disclosed and still obtain a like or similar result without departing from the spirit and scope of the invention.

EXAMPLE 1

Preparation of Antimicrobial Solutions

A process was performed essentially in accordance with U.S. Pat. No. 5,624,704. Briefly, in a dark glass bottle, 40 ml of methanol was heated to about 45 deg.C on a magnetic stirrer-hot plate and 0.2 g of sodium hydroxide was dissolved therein. Heating was removed and 5 g minocycline, 8 g rifampin, and 80 ml butyl acetate, were dispersed in the solvent. 20 ml aliquots of the mixture were transferred to glass beakers containing either a pre-weighed polyethylene terepthalate sewing cuff assembly (Carbomedics Prosthetic Heart Valve, CPHV™ 27 Mitral) or a polytetrafluoroethylene felt ring (27 Mitral), prepared at Sulzer Carbomedics Inc. (Austin, Tex.). The samples were incubated in the antimicrobial solutions for approximately 1.5 hours at about 45 deg.C. After incubation, the treated cuffs and felts were removed from the antimicrobial solution and air-dried overnight. After drying, each sample was weighed and transferred to a sterile bag. Exposure to light was minimized during and after the drying process until further studies were performed.

In an illustrative process according to the present invention, 2000 ml of methanol was added to a dark glass bottle and heated to about 45 deg.C on a magnetic stirrer-hot plate. 5 g minocycline and 8 g rifampin were dispersed in the methanol. 20 ml aliquots of the mixture were transferred to glass beakers containing either a pre-weighed polyethylene terepthalate sewing cuffs (CPIIV™ 27 Mitral) or a polytetrafluoroethylene felt ring (27 Mitral), prepared at Sulzer Carbomedics Inc. The samples were incubated in the antimicrobial solutions for approximately 1.5 hours at about 45 deg.C. After incubation, the treated cuffs and felts were removed from their respective solutions and air-dried overnight. After drying, each sample was weighed and transferred to a sterile bag. Sample exposure to light was minimized during and after the drying process.

Table 1 below compares the formulations of the antimicrobial solutions used in producing minocycline/rifampin sewing cuffs and felts in accordance with either U.S. Pat. No. 5,624,704, or according to an illustrative example of the present invention. The antimicrobial solutions prepared according to U.S. Pat. No. 5,624,704 contained antimicrobial agents, an alkalinizing agent (e.g., sodium hydroxide), an organic solvent (e.g., methanol), and a penetrating agent (e.g., butyl acetate). In contrast, the illustrative antimicrobial solution of this invention contained only the antimicrobial agents dissolved in solvent (e.g., methanol).

TABLE 1

COMPARISON OF FORMULATIONS USED

| REAGANTS | U.S. Pat. No. 5,624,704 | PRESENT INVENTION |
| --- | --- | --- |
| Sodium Hydroxide | 0.1% w/v | 0% |
| Methanol | 20% v/v | 100% v/v |
| Butyl Acetate | 80% v/v | 0% |
| Rifampin | 4% w/v | 4% w/v |
| Minocycline | 2.5% w/v | 2.5% w/v |

EXAMPLE 2

Antimicrobial Agent Incorporation

Antibiotic incorporation into or onto the sewing cuff and felt samples was monitored by determining the change in mass before and after incorporation, and also by high-performance liquid chromatography (HPLC) analysis. For HPLC analysis, the dried samples were placed in glass beakers containing 30 ml of methanol, and this extraction solution was sonicated for about 30 minutes. The supernatant was poured into a dark glass jar. The extraction process was repeated up to three times and the extracts were combined and analyzed by HPLC using a Beckman Nouveau Gold HPLC system (Beckman Instruments; Fullerton, Calif.). The samples were diluted as necessary and injected in 0.1 M sodium phosphate, pH 3.2. 25 ul of each sample was injected by an auto sampler into the HPLC system. Sample separation was achieved using acetonitrile:water (4:6 v/v), with a flow rate of 1 ml/min, using a Water's C18 Nova Pak 60A, 4 um, 3.9×150mm column, maintained at about 30 deg.C. Ultraviolet detection at 339 nm detected the minocycline and rifampin peaks at about 1.4 and 4.0 minutes, respectively, under these conditions. A calibration curve was generated using 1:1 mixtures of minocycline and rifampin in the mobile phase at a concentration range between 1 ug/ml and 100 ug/ml.

Table 2 below summarizes the results for total antibiotic incorporation into the sewing cuffs and felts treated according to U.S. Pat. No. 5,624,704, and according to the present invention. From these results, it is apparent that the method of the present invention achieves levels of antibiotic incorporation into the sewing cuffs and felts comparable to those observed for the method of U.S. Pat. No. 5,624,704. For the HPLC analysis, total incorporation values were calculated by adding the weight values obtained for minocycline and rifampin. The cuffs generally had higher loading compared with the felts, possibly due to the greater mass and surface area associated with the polyester material. The values obtained by the HPLC method were slightly lower compared with the values obtained by the total mass method. This may be attributed to the extraction method employed for HPLC sample preparation, which may not have been complete.

TABLE 2

ANTIBIOTIC INCORPORATION IN SEWING CUFFS AND FELTS

| SAMPLES | TOTAL LOADING BY WEIGHT (mg) | TOTAL LOADING BY HPLC (mg) |
| --- | --- | --- |
| Cuff (U.S. Pat. No. 5,624,704 | 112 | 105 |
| Cuff (methanol only) | 115 | 91 |
| Felt (U.S. Pat. No. 5,624,704) | 51 | 81 |
| Felt (methanol only) | 48 | 43 |

Ultraviolet spectra of minocycline and rifampin obtained during HPLC analysis demonstrated that they have distinctive $\text{lambda}_{max}$ values of 350 and 334, respectively. The spectral properties observed did not change as a result of incorporation method (not shown), indicating that the compounds maintained their structure during the medical device treatment processes.

EXAMPLE 3

Release Profiles for Rifampin and Minocycline

The kinetics of antibiotic release from the treated samples was evaluated by incubating the samples in 15 ml phosphate buffered saline (PBS) at about 37 deg.C for 30 days. For about the first hour, the samples were gently agitated in PBS at room temperature in 15 ml PBS. This PBS solution was removed and frozen until further analysis. Fresh PBS was added and the samples were placed in a 37 deg.C incubator. the PBS was thereafter replaced at 1, 2, 4, 5, 7, 11, 15, 21, 25, and 30 days, and each aliquot was frozen until subsequent analysis by HPLC. The release profiles for rifampin and minocycline are summarized below in Tables 3 and 4, respectively.

TABLE 3

RELEASE OF RIFAMPIN (mg) OVER 30 DAYS

| Day collected | Cuff (U.S. Pat. No. 5,624,704) | Cuff (methanol only) | Felt (U.S. Pat. No. 5,624,704) | Felt (methanol only) |
|---|---|---|---|---|
| 0 | 14.0 | 14.6 | 10.6 | 5.85 |
| 1 | 22.1 | 19.9 | 12.7 | 13.5 |
| 2 | 13.4 | 13.1 | 2.16 | 5.63 |
| 4 | 5.37 | 10.1 | 0.66 | 1.31 |
| 5 | 0.72 | 2.45 | 0.25 | 0.12 |
| 7 | 0.29 | 0.59 | 0.16 | 0.02 |
| 11 | 0.25 | 0.20 | 0.08 | 0.01 |
| 15 | 0.20 | 0.06 | 0.04 | — |
| 21 | 0.17 | 0.02 | 0.02 | — |
| 25 | 0.13 | 0.02 | 0.01 | — |
| 30 | 0.07 | 0.01 | — | — |
| Avg. Total | 56.51 | 60.49 | 53.25 | 26.44 |

TABLE 4

RELEASE OF MINOCYCLINE (mg) OVER 30 DAYS

| Day collected | Cuff (U.S. Pat. No. 5,624,704) | Cuff (methanol only) | Felt (U.S. Pat. No. 5,624,704) | Felt (methanol only) |
|---|---|---|---|---|
| 0 | 11.6 | 15.8 | 8.25 | 4.8 |
| 1 | 7.43 | 8.70 | 3.53 | 0.75 |
| 2 | 2.18 | 1.13 | 0.33 | 0.1 |
| 4 | 0.92 | 1.01 | 0.11 | 0.02 |
| 5 | 0.15 | 0.09 | 0.05 | — |
| 7 | 0.05 | 0.06 | 0.05 | — |
| 11 | 0.05 | 0.03 | 0.02 | — |
| 15 | 0.04 | 0.02 | — | — |
| 21 | 0.08 | — | — | — |
| 25 | 0.02 | — | — | — |
| 30 | 0.01 | — | — | — |
| Avg.Total | 22.1 | 25.3 | 24.7 | 11.9 |

From the above examples, it is apparent that minocylcine and rifampin can be incorporated into medical devices according to the method of this invention without the need to include the penetrating agents and/or alkalinizing agents taught by U.S. Pat. No. 5,624,704 as necessary for effective antimicrobial agent incorporation. Moreover, the devices exhibited clinically desirable antimicrobial agent release characteristics.

EXAMPLE 4

Inhibition of Device Colonization and Infection in Vivo

Samples of polyethylene terepthalate fabric (DTH-2, Vascutek Inc., Renfrewshire, Scottland) were sewn around polytetrafluoroethylene felt (CR Bard Inc., Haverhill, Mass.) using silicon-treated, non-absorbable, braided polyester 4.0 sutures (Davis and Geck Inc., St.Louis, Mo.). Some of these sample assemblies were treated according to U.S. Pat. No. 5,624,704 by contacting them with a solution comprised of 40 mg/ml rifampicin, 25 mg/ml minocycline, and I mg/ml sodium hydroxide in 20% (v/v) methanol in butyl acetate. Other sample assemblies were treated with 40 mg/ml rifampicin and 25 mg/ml minocycline dissolved in methanol only. The samples were incubated in these solutions for approximately 1.5 hours at about 45 deg.C. After incubation, the samples were removed from their respective solutions and air-dried overnight.

The treated samples were inoculated with approximately $10^5$ CFU Staphylococcus aureus (P1 strain, a mutant of ATCC 25923), and implanted subcutaneously into rabbits. The samples were retrieved from the animals after one week after implantation. Device colonization was evaluated by culturing the retrieved device by rolling and/or dragging each side of the device on chocolate agar plates (BBL Media, Becton Dickinson Microbiology Systems, Cockeysvile, Md.). Device-related infection was evaluated by inoculating blood samples taken at the time of device retrieval on chocolate agar plates. Bacterial growth was assessed after incubating the plates for 48 hours at 37 deg.C. The results of these experiments are summarized in Table 5 below.

|  | Untreated | U.S. Pat. No. 5,624,704 | Methanol only |
|---|---|---|---|
| Device Colonization | 25/31 | 2/30 | 1/34 |
| Device-related Infection | 25/31 | 0/30 | 0/34 |

These results demonstrate the in vivo efficacy of medical devices treated in accordance with this invention. In particular, protection from device colonization and device-related infection was comparable, if not improved, relative to a group of samples treated according to U.S. Pat. No. 5,624,704.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for treating an implantable medical device, comprising:
   (1) dissolving at least one antibiotic agent in a solvent consisting of methanol to form an antimicrobial solution;
   (2) providing an implantable medical device comprising a polymer fabric;
   (3) contacting the antimicrobial solution with at least a portion of the polymer fabric, under conditions effective for causing incorporation of at least some of the antibiotic agent into said polymer fabric; and
   (4) incorporating heparin into a least a portion of the medical device.

2. The method of claim 1, wherein said fabric is selected from the group consisting of dacron fabric, polytetrafluoroethylene fabric, polyethylene terephthalate fabric, and nylon fabric.

3. The method of claim 1, wherein the medical device is comprised of polytetrafluoroethylene, polyethylene terepthalate, polyurethane, silicon rubber, polyethylene, cancellous titanium or hydroxyapatite.

4. The method of claim 1, wherein the medical device is selected from the group consisting of annuloplasty rings, heart valve sewing cuffs, catheter sewing cuffs, pericardial patches, vascular grafts, sutures, pledgets, and wound dressings.

5. The method of claim 1, wherein said contacting step comprises dipping, injecting, flushing, or spraying the antimicrobial solution into or onto the polymer fabric.

6. The method of claim 1, wherein the antimicrobial solution is contacted with the polymer fabric for a duration in the range of about 0.1 hour to about 2 hours.

7. The method of claim 1, wherein the antimicrobial solution that is contacted with the polymer fabric has a temperature in the range of about 10 deg.C to about 60 deg.C.

8. The method of claim 1, wherein the concentration of the antibiotic agent in the antimicrobial solution is in the range of about 1 mg/ml to about 60 mg/ml.

9. The method of claim 1, further comprising removing substantially all of said methanol after said antibiotic agent is incorporated into the polymer fabric.

10. The method of claim 1, wherein the heparin is covalently bonded to the medical device.

11. A method for treating an implantable medical device, comprising:
(1) dissolving two or more antibiotic agents in a solvent consisting of methanol to form an antimicrobial solution;
(2) providing an implantable medical device comprising a polymer fabric;
(3) contacting the antimicrobial solution with at least a portion of the polymer fabric, under conditions effective for causing incorporation of at least some of the said antibiotic agents into said polymer fabric; and
(4) incorporating heparin into at least a portion of the medical device.

12. The method of claim 11, wherein the medical device is comprised of polytetrafluoroethylene, polyethylene terepthalate, polyurethane, silicon rubber, polyethylene, cancellous titanium or hydroxyapatite.

13. The method of claim 11, wherein the medical device is selected from the group consisting of annuloplasty rings, heart valve sewing cuffs, catheter sewing cuffs, pericardial patches, vascular grafts, sutures, pledgets, and wound dressings.

14. The method of claim 11, wherein said contacting step comprises dipping, injecting, flushing, or spraying the antimicrobial solution into or onto the polymer fabric.

15. The method of claim 11, wherein the antimicrobial solution is contacted with the polymer fabric for a duration in the range of about 0.1 hours to about 2 hours.

16. The method of claim 11, wherein the antimicrobial solution that is contacted with the polymer fabric has a temperature in the range of about 10 deg.C to about 60 deg.C.

17. The method of claim 11, wherein the concentration of the antibiotic agent in the antimicrobial solution is in the range of about 1 mg/ml to about 60 mg/ml.

18. The method of claim 1, further comprising removing substantially all of said methanol after said antibiotic agent is incorporated into the polymer fabric.

19. The method of claim 11, wherein said heparin is covalently bonded to the medical device.

20. The method of claim 11, wherein said heparin is ionically bonded to the medical device.

* * * * *